United States Patent [19]

Bruce

[11] Patent Number: 4,879,654
[45] Date of Patent: Nov. 7, 1989

[54] DRILLING FLUID

[75] Inventor: Sue Bruce, Huntingdon, England

[73] Assignee: Schlumberger Technology Corporation, Houston, Tex.

[21] Appl. No.: 150,815

[22] Filed: Feb. 1, 1988

[30] Foreign Application Priority Data

Feb. 10, 1987 [GB] United Kingdom ................ 8702920

[51] Int. Cl.$^4$ ........................ E21B 21/08; G01N 9/04
[52] U.S. Cl. ...................................... 364/422; 175/48; 73/434
[58] Field of Search ................ 364/422; 73/434, 61.4, 73/153; 175/48, 65, 40

[56] References Cited

U.S. PATENT DOCUMENTS

| 4,091,881 | 5/1978 | Manus | 175/48 |
| 4,195,527 | 4/1980 | Ebeling et al. | 73/434 |
| 4,570,480 | 2/1986 | Fontenot et al. | 175/48 |
| 4,588,035 | 5/1986 | Van Gibs et al. | 175/48 |
| 4,653,597 | 3/1987 | Johnson | 175/48 |
| 4,677,851 | 7/1987 | McAuley | 73/434 |
| 4,745,807 | 5/1988 | O'Neill | 73/434 |

OTHER PUBLICATIONS

"Borehole Stability Analysis"; a GeoSource Ltd. brochure, Letter to T. Mazelek dated Mar. 31, 1989.

Primary Examiner—Jerry Smith
Assistant Examiner—Kim Thanh Tbui
Attorney, Agent, or Firm—Stephen L. Borst

[57] ABSTRACT

A drilling fluid to be circulated through a borehole as it is drilled is produced by mixing solid and liquid drilling fluid components in such proportions that the density of the fluid has a selected value which lies between upper and lower limits (c) calculated for all depths of the borehole to be drilled. The lower limits satisfy a shear failure criterion for the material forming the wall of the borehole and above which influx of pore fluid does not occur, and the upper limits satisfy either the same shear failure criterion or a tensile failure criterion, depending on which of the two criteria predicts the lower upper limit. Upper and lower shear failure values (b) are calculated as a function of depth and tensile failure values (a) are calculated as a function of depth. The calculations include determining the in-situ stress state at the site of the borehole, and calculating the stresses which will occur at the borehole wall as a function of depth and drilling fluid density.

9 Claims, 7 Drawing Sheets

DRILLING FLUID

This invention relates to the production of drilling fluid, and especially, but not exclusively, to a method of determining a safe value of density for a drilling fluid to be circulated through a borehole.

When a borehole is being drilled to tap an oil or gas field, a liquid mixture, known as drilling fluid or mud, is passed into the borehole to flush out cuttings made by the drill bit and to support the walls of the borehole. The mud is usually a mixture of water, a thixotropic viscosifier such as clay, a weighting material such as barite, and certain chemicals chosen, for example, to maintain chemical stability of the material being drilled through. A small proportion of oil may be added to the water, or an oil-water emulsion or oil alone may be used instead of water. A principal purpose of the viscosifier is to ensure that the cuttings stay in suspension. The weight of barite in the mud helps to prevent matter from falling away from the side wall of the borehole. Such falling away of matter is known as sloughing.

At any point in the earth there is a vertically directed force due to the weight of material above that point. The vertically directed force per unit horizontal area is referred to as vertical in-situ stress. Ignoring the atmospheric pressure at the place considered, the vertical in-situ stress $\sigma_{zz}$ at a true vertical depth z below the surface of the earth at the place considered can be calculated from $$\sigma_{zz}(z) = \int_{0}^{z} \rho_b g \, dz$$

where g is the acceleration due to gravity and $\rho_b$ is the bulk density over the depth z concerned and may vary with depth, i.e., $\rho_b$ may be a function of z. In practice, bulk density may be measured in a borehole by equipment such as the Schlumberger FDC Formation Density Compensated tool or LDT Litho-Density tool. If no or only some measurments of $\rho_b$ are available, a constant value of, for example, 2.305 gm/cm$^3$, may be assumed. Different constant values are known to be appropriate in different places.

Horizontal stresses occur naturally in the earth due to the compression of inner layers by the weight of outer layers of rock. Tectonic movement of tectonic plates may also create lateral stresses. Stress in a horizontal plane is usually different in different directions in the plane.

The mud passed into a borehole exerts a hydrostatic pressure which depends in the usual way on its density so that the pressure exerted radially on the walls of the borehole at a true vertical depth z by the mud is given by the product $\rho_m g z$ where $\rho_m$ is the density of the mud, if atmospheric pressure is ignored. It is known that unless the density of the mud is correct, problems, some potentially catastrophic, will arise in the drilling of a borehole. The problems that can arise are:

fracturing of the borehole wall;

sloughing or caving in to such an extent that the amount of rock falling into the hole cannot be carried out by the mud, or that a large amount of cement is required in setting casing in the borehole, or the borehole diameter becomes so large that downhole measurements cannot be carried out or interpreted easily or reliably;

and influx of fluid from rock pores.

The last of these problems is potentially catastrophic since the pore fluid may be gas and can result in a blow out. A borehole in which there is an influx of fluid from the drilled formations is said to take a kick.

It is known that if mud density is too low, a kick may be taken, and that if it is too high the borehole wall may fracture at some level, and also that it must remain within upper and lower limits to prevent excessive sloughing or caving in.

Sloughing and caving in of borehole wall is attributed to shear failure of the wall. Those skilled in the art will understand that the occurence of shear failure in rock which is subject to orthogonal direct stresses relates to the difference between the size of compressive or tensile stress in one direction in the rock and the size of compressive or tensile stress in another direction and the size of compressive or tensile stress in another direction in the rock exceeding a value which is characteristic of the particular rock material concerned.

Where a borehole is drilled, a column of rock is replaced by a column of mud and the stresses in the rock at the wall of the borehole are altered by the difference between those in the replaced rock and those in the mud which now occupies the borehole. Except near the earth surface, the vertical stress in the rock of the wall of a vertical hole is usually the greatest principal stress. The other principal stresses in the wall are the radial stress, which is opposed to the hydrostatic pressure exerted by the mud, and the hoop or tangential stress acting horizontally circumferentially around the borehole. If the mud density is too low, the difference between the radial stress and the vertical stress leads to shear failure of the wall. If the mud density is too high, the tangential stress becomes too low, and the difference between the vertical and tangential stresses leads to shear failure.

Fracturing of a borehole, i.e., tensile failure of the wall of the borehole at a particular depth, may be compared to the snapping of an elastic band when the band is forced to expand to surround an object and is thereby stretched to the extent that it breaks. In such a case, the density of the mud is so high that the pressure exerted radially outwards by the mud at a particular depth stretches the encircling borehole wall to the extent that the material of the wall breaks under the tensile stress induced. The pressure at which the break begins is known as the fracture initiation pressure. At this pressure a crack initiates and propagates away from the borehole, mud being lost into the crack.

Fracturing of the borehole wall can be an expensive event because of the loss of mud, and is dangerous because of the risk of influx of pore fluid.

Hitherto, the density of mud to be used in drilling a new borehole has been chosen on the basis of consideration of the mud densities successfully used in neighboring boreholes, if any, and the collective experience of the drilling organization personnel. For example, if a borehole has been drilled nearby, and a kick was taken or sloughing was excessive, a higher density will be chosen.

The drilling of deviated boreholes, i.e., boreholes having their axes at an angle to the vertical, is particularly a matter of trial and error since conventional practice is to use the same mud density as has been used successfully in a nearby, usually vertical, borehole, or to use a mud with a higher density, the increase in density being guesswork on the part of the drilling personnel.

It is accordingly an object of the present invention to provide a method of determining the density of drilling fluid to be used to avoid fracturing the borehole wall.

It is another object of the invention to provide a method of determining the density of drilling fluid to be used to avoid hole instability problems arising from sloughing or caving in of the borehole wall.

Yet a further object of the present invention is to provide a method of producing drilling fluid having a density such that when the drilling fluid is circulated in a predetermined borehole, stability and integrity of the borehole wall is maintained.

According to one aspect of the present invention there is provided a method of determining a safe value of density for a drilling fluid to be circulated through a borehole during drilling of the borehole, the method comprising the steps of determining the in-situ stress state at the site of the borehole, calculating the stresses which will occur at the borehole wall as a function of depth and drilling fluid density when the borehole is drilled, calculating pore pressure as a function of depth, determining the values of drilling fluid density as a function of depth which satisfy tensile and shear failure criteria of the material forming the borehole wall, calculating a drilling fluid density value which gives a drilling fluid pressure equal to the pore pressure as a function of depth, selecting the lower of two higher values of drilling fluid density as a function of depth which satisfy one or the other failure criterion, selecting the higher of two lower values of drilling fluid density as a function of depth which respectively satisfy the shear failure criterion and give a drilling fluid pressure equal to the pore pressure, and selecting a drilling fluid density value which lies between the selected higher value and lower value for substantially all values of the depth.

According to another aspect of the invention there is provided a method of producing drilling fluid, comprising mixing solid and liquid drilling fluid components in such proportions as to provide a drilling fluid having a density which lies between upper and lower values calculated for all depths of a borehole to be drilled, the said upper and lower values being the closest such values to satisfy one or the other of a tensile failure criterion and a shear failure criterion for the material forming the wall of the borehole and prevent influx of pore fluid.

According to a further aspect of the invention there is provided a method of drilling a borehole comprising circulating a drilling fluid through the borehole as it is drilled, the density of the drilling fluid being maintained at a calculated value such that the stresses at the cylindrical wall of the borehole are maintained at values which prevent tensile and shear failure of the material of the said wall and influx of pore fluid.

The invention will now be described in more detail, solely by way of example, with reference to the accompanying drawings in which:

FIGS. 5a-c, 6a-c 7a-c are examples of three track logs obtained in accordance with the present invention.

Figure 1:
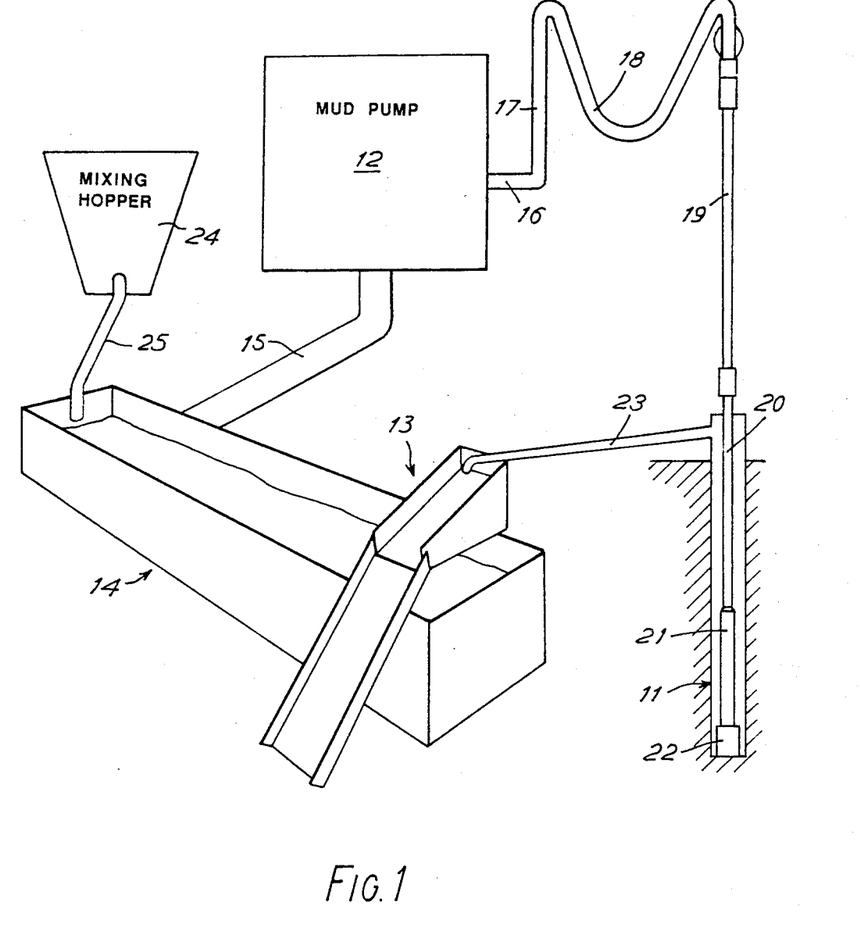
FIG. 1 is a schematic representation of a mud circulation system for a borehole.

FIG. 1 shows a circulation system for drilling fluid, i.e., mud, including a borehole 11, a mud pump unit 12, a shale shaker 13 and mud pits 14. The mud pump unit 12 draws mud through a suction line 15 from the mud pits 14 and forces the mud through a discharge line 16, a standpipe 17, a rotary hose 18, a kelly 19, a drill pipe 20, and a drill collar 21 to a drill bit 22 where the mud exits to the borehole 11. The flowing mud occupies the space between the drill components forming the drill string and the cylindrical wall of the borehole, this space being known as the annulus. An exit for the flowing mud is provided at the top of the borehole 11 from which the mud passes through a mud return line 23 to a vibrating screen device which is the shale shaker 13 where drill cuttings are screened out of the mud and the mud is returned to the mud pits 14.

The mud is initially made up in the mud pits and its composition can be adjusted during circulation. Solid materials used in forming or adjusting the mud composition are added from a mud-mixing hopper 24 having an outlet 25 to the mud pits 14. Agitators (not shown) are provided at the mud pits to keep the mixture of solid and liquid components uniform. Desilters (not shown) and desanders (not shown) may be included in the flow path between the borehole 11 and the mud pits 14 to remove fine particles produced by the drilling which would pass through the screen of the shale shaker 13.

In accordance with the invention, the composition of the mud is determined and maintained such that the mud density is within upper and lower limits, the upper limit being a density below which neither fracturing of the borehole wall nor excessive sloughing occurs, and the lower limit being a density above which excessive sloughing does not occur and above which a pore fluid influx does not occur. To determine these limits, the in-situ stress state of the earth where the borehole is to be drilled is determined, the stresses occuring at the borehole wall as a function of mud density are determined, and the wall stresses are compared with selected failure criteria. Pore pressure is calculated from pore fluid density, which may be assumed to be constant, typically at the density of water, or may be known from measurements.

Determination of the in-situ stress state

A vertical in-situ stress exists at a point in the earth because of the weight of rock above that point. The value of this stress can be calculated from the equation cited hereinbefore:

$$\sigma_{zz}(z) = \int_0^z \rho_b g \, dz$$

If there is a nearby borehole from which a log of bulk density $\rho_b$ has been obtained by means of for example, a Schlumberger FDC Formation Density Compensated tool or an LDT Litho-Density tool, the bulk density $\rho_b$ can be treated as a function of true vertical depth z. In the absence of measured values, $\rho_b = 2.305$ g/cm$^3$ can be assumed. If the available bulk density log is specified relative to a downhole depth which is not the true vertical depth, for example, pipe depth, a suitable conversion must be effected before the integration is carried out. The conversion makes use of survey data for the logged borehole from for example a directional survey tool to identify the borehole trajectory. If there is no survey data but the logged borehole is assumed to be vertical in practice, then the log depth is taken to be true vertical depth.

If a measured value of vertical stress is available for a particular depth d, the calculated vertical stress is calibrated by multiplying all calculated stresses by the ratio of the measured vertical stress at the particular depth d, to the calculated vertical stress at that depth d.

In the absence of any information that the two horizontal principal stresses are different, they are assumed to be equal. The horizontal stress state is then attributed entirely to the effect of the vertical stress, which appears as the result of the vertical gravitational compression on the solid rock materials and on the pore fluids. It is assumed that the rock is linearly poro-elastic.

A linearly poro-elastic material in which pore pressure $p_p$ is constant and the bulk modulus of the solid constituent of the material is infinite obeys six equations of the form:

$$-\frac{E}{1+v} \epsilon_{ij} = (\sigma_{ij} - P_p \delta_{ij}) - \frac{v}{1+v} (\sigma_{kk} - 3p_p)\delta_{ij}$$

in which i and j each take the values 1 to 3, so there is an equation for $\epsilon_{11}$, a separate equation for $\epsilon_{12}$ etc., and in which summations are observed for repeated indices. This means there are nine equations in total, but symmetry consideratons mean that some of the equations are identicl and the number of independent equations is six.

In addition, the three static equilibrium equations obeyed are:

$$\frac{\partial \sigma_{ij}}{\partial x_j} = 0.$$

in which i can take values 1 to 3. In the above equations E is Young's modulus, $v$ is Poisson's ratio, $\epsilon_{ij}$ are strains, $p_{ij}$ are stresses, $\delta_{ij}$ is the Kronecker delta (which equals 1 if i=j and equals 0 if i≠j), and x is a Cartesian space vector.

The value of horizontal stress is calculated from the classical or Terzaghi equation:

$$\sigma_{xx}^\infty = \sigma_{yy}^\infty = \frac{v}{1-v} (\sigma_{zz}^\infty - p_p) + p_p$$

where $\sigma_{zz}^\infty$ is the vertical principal stress calculated as $\sigma_{zz}$ hereinbefore. The superscript $\infty$ is used to indicate that the value concerned is the in-situ or farfield stress.

Poisson's ratio $v$ for the solid rock materials is calculated from shear and compressional sonic velocities obtained by logging a nearby well by using, for example, a Schlumberger long spacing sonic tool operated with waveforms recorded, or a Schlumberger digital sonic tool. Poisson's ratio $v$ is then calculable from $$v = \frac{0.5 \,(dtsm/dt)^2 - 1}{(dtsm/dt)^2 - 1}$$

where dtsm is the measured acoustic shear-wave travel time, and dt is the measured acoustic compressional-wave travel time, as described for example in Mechanical Properties Evaluation and its Applications by David Edwards, published by Schlumberger Technical Services Inc., Europe Unit, Interpretation Development December 1985, EUR-85001.

If compressional sonic velocity data is not available, a value of 311.7 µs/m is assumed for dt.

If shear sonic velocity data is not available, Poisson's ratio is assumed to have a value of 0.25, or dtsm is assumed to be 541.3 µs/m.

If measured values of Poisson's ratio are available from drill cores obtained from particular depths, these measured values are used to calibrate the values calculated from the expression for $v$ given hereinbefore. Calibration is advantageous because $v$ calculated from acoustic data may differ from a statically measured value of $v$, and the static value is the more relevant value in calculating horizontal stress from vertical stress and in calculating stresses at a borehole wall. The calibration is preferably performed by multiplying the calculated values of $v$ by the ratio of the measured value of $v$ at depth d to the calculated value of $v$ at depth d.

Pore pressure $p_p$ is calculated from an assumed gradient of 0.0105 MPa per meter of true vertical depth. If a measured value of $p_p$ is available for any particular depth, the measured value is used to calibrate the calculated values. Measured values of pore pressure $p_p$ may be available from a Schlumberger RFT Repeat Formation Tester tool or a production test, for example.

If a measured value of horizontal stress is available, it is used to calibrate the calculated values. Such calibration is advantageous because the assumption of zero tectonic stress may be false, and acoustic velocity data used in calculating values of Poisson's ratio $v$ may be inaccurate. The calibration is performed by calculating the horizontal strain during burial of rock at the depth considered, which is the depth for which a measured horizontal stress and a calculated vertical stress are available, and assuming that this calculated horizontal strain has occurred at every depth.

Measured values of horizontal stress can be obtained from a micro-fracture process, or a differential strain curve analysis, or a strain relaxation analysis.

In a micro-fracture process, the fluid pressure in a nearby borehole is intentionally increased until a fracture is propagating away from this borehole. The minimum horizontal in-situ stress is determined as the pressure in the fluid in the borehole at the point at which the fracture closes on reducing the pressure.

In differential strain curve analysis, an oriented rock core retrieved from a nearby borehole is equipped with strain gauges and loaded in the laboratory. The three components of in-situ stress are determined from the points of closure of internal microcracks which were generated during the retrieval of the core from the borehole.

In strain relaxation analysis, an oriented core freshly retrieved from a nearby borehole is equipped with strain gauges and the three in-situ stresses are determined by monitoring the anelastic deformation of the core.

If measured values of both principal horizontal stresses are obtained for one particular depth, it is assumed that the difference between the horizontal stresses scales linearly with depth starting from zero at the earth surface. If measured values of both principal horizontal stresses are available for several depths, the scaling with depth is modified appropriately.

When a borehole is being drilled, rock which was originally in the borehole is replaced by mud. The replacement by mud usually disturbs the in-situ stress state immediately about the borehole. The replaced column of rock supported three, probably different, principal stresses. The column of mud exerts three principal stresses which are equal at any particular depth and are usually less than the stress in the replaced rock column.

The stresses arising in the immediate vicinity of the borehole containing mud can be calculated with the assumptions of a linear elastic rock and pore pressure which is constant at a value found at points distant from the borehole, or with the use of a full, time-dependent Biot poro-elastic constitutive equation for the rock, the assumption of constant pore pressure at a far field value being abandoned. Other alternative calculation methods are the use of the standard modern extended version of the full Biot constitutive equations which allows for pore fluid compressibility, as given by R. N. Chandler and D. L. Johnson in the Journal of Applied Physics, Volume 52, page 3391, published in 1981, or the use of a poro-elastic plastic constitutive equation.

Calculation of stressees that occur at a borehole wall

An example of the mathematical basis of the calculation of the mud pressure at which a deviated borehole will fail in tension or compression will now be described. The rock is modelled as a poro-elastic solid in which the pore pressure is constant.

The sensitivity of "safe" mud pressure values to the compressive failure criterion, hole deviation and in-situ horizontal stress is considered. The calculation is useful when 1. the horizontal in-situ earth stress is known with reasonable accuracy,
2. the rock deformation is known to be described by a poro-elastic model, and
3. the rock failure criteria are known.

Symbols used in the calculation will now be listed together with their definitions.

| | |
|---|---|
| $\underline{\sigma}^\infty$ | Stress tensor which describes in-situ stress state with respect to a Cartesian coordinate frame in which the z-axis is vertical and the x-axis is in the direction of the greater horizontal principal stress. |
| $\underline{\Sigma}^\infty$ | Stress tensor which describes in-situ stress state with respect to a Cartesian coordinate frame in which the z-axis lies along the borehole and the x-axis lies in the same vertical plane as the borehole. |
| $\underline{\Sigma}$ | Stress tensor which describes the stress state around the borehole with respect to cylindrical polar axes, $\theta$, r, z, the z-axis of which lies along the borehole whilst $\theta = 0$ corresponds to the x-axis of $\underline{\Sigma}^\infty$. |
| $\Psi$ | Borehole deviation |
| $\phi$ | Angle between a vertical plane through the borehole and a vertical plane through the x-axis of $\sigma^\infty$ |
| a | Borehole radius |
| $p_w$ | Mud pressure |
| $p_p$ | Pore pressure |
| $C_o$ | Rock compressive strength |
| q | $\tan^2\left(\frac{\pi}{4} + \frac{\phi}{2}\right)$ where $\phi$ is the angle of internal friction |
| E | Young's Modulus |
| $\nu$ | Poisson's ratio |
| $\epsilon$ | Strain tensor |
| superscript $\infty$ | In-situ or far field state |
| dt | compressional sonic travel time |
| dtsm | shear sonic travel time |
| g | acceleration due to gravity |
| $K_b$ | bulk modulus |
| T | tensile strength |
| $V_{clay}$ | volume fraction of clay |
| $\sigma_1$ | maximum principal stress |
| $\sigma_2$ | intermediate principal stress |
| $\sigma_3$ | minimum principal stress |
| $\sigma_{xx}^\infty$ | horizontal principal in-situ stress along the x axis |
| $\sigma_{yy}^\infty$ | horizontal principal in-situ stress along the y axis |
| $\sigma_{zz}^\infty$ | vertical principal in-situ stress |
| $\mu$ | coefficient of internal friction |
| $\phi$ | angle of internal friction |
| $\rho_b$ | bulk density |

It will be noted that $$p_w = \rho_m g d$$

where $\rho_m$ is mud density and d is true vertical depth.

Let $(\sigma_{xx}^\infty, \sigma_{yy}^\infty, \sigma_{zz}^\infty)$ be for the far field (in-situ) principal stresses, with $\sigma_{zz}^\infty$ the vertical component of stress and $\sigma_{xx}^\infty \leq \sigma_{yy}^\infty$ (compressive stresses positive).

Consider a deviated borehole. Suppose this borehole to be a smooth cylinder of circular cross-section drilled at an angle $\Psi$ to the vertical and such that a vertical plane through the borehole is at an angle $\phi$ to a vertical plane through the x-axis.

The in-situ stress state $\underline{\sigma}^\infty$ may be described with respect to a Cartesian coordinate frame in which the z-axis lies along the borehole and the x-axis lies in the same vertical plane as the borehole.

$$\Sigma^\infty_{xx} - p_p = \cos^2\psi \cos^2\phi\,(\sigma_{xx}^\infty - p_p) + \cos^2\psi \sin^2\phi\,(\sigma_{yy}^\infty - p_p) + \sin^2\psi\,(\sigma_{zz}^\infty - p_p)$$

$$\Sigma^\infty_{yy} - p_p = \sin^2\phi\,(\sigma_{xx}^\infty - p_p) + \cos^2\phi\,(\sigma_{yy}^\infty - p_p)$$

$$\Sigma^\infty_{zz} - p_p = \sin^2\psi \cos^2\phi\,(\sigma_{xx}^\infty - p_p) + \sin^2\psi \sin^2\phi\,(\sigma_{yy}^\infty - p_p) + \cos^2\psi\,(\sigma_{zz}^\infty - p_p)$$

$$\Sigma^\infty_{xy} = -\cos\psi \cos\phi \sin\phi\,(\sigma_{xx}^\infty - p_p) + \cos\psi \sin\phi \cos\phi\,(\sigma_{yy}^\infty - p_p)$$

$$\Sigma^\infty_{xz} = \cos\psi \sin\psi \cos^2\phi\,(\sigma_{xx}^\infty - p_p) + \cos\psi \sin\psi \sin^2\phi\,(\sigma_{yy}^\infty - p_p) - \sin\psi \cos\psi\,(\sigma_{zz}^\infty - p_p)$$

$$\Sigma^\infty_{yz} = -\sin\phi \cos\phi \sin\psi\,(\sigma_{xx}^\infty - p_p) + \cos\phi \sin\phi \sin\psi\,(\sigma_{yy}^\infty - p_p)$$

Let $\underline{\Sigma}$ describe the stress state around the borehole with reference to cylindrical polar axis $\theta$, r, z, the z-axis of which lies along the borehole axis. If the pore pressure is assumed constant at the far field value, and the variation of stresses along the borehole is considered negligible relative to radial and tangential variations, the stress state is given by $$\Sigma_{rr} - p_p = \left(\frac{\overset{\infty}{\Sigma}_{xx} - p_p + \overset{\infty}{\Sigma}_{yy} - p_p}{2}\right)\left(1 - \frac{a^2}{r^2}\right) +$$

$$\left(\frac{\overset{\infty}{\Sigma}_{zz} - \overset{\infty}{\Sigma}_{yy}}{2}\right)\left(1 + \frac{3a^4}{r^4} - \frac{4a^2}{r^2}\right)\cos 2\theta +$$

$$\overset{\infty}{\Sigma}_{xy}\left(1 + \frac{3a^2}{r^4} - \frac{4a^2}{r^2}\right)\sin 2\theta + (p_w - p_p)\frac{a^2}{r^2}$$

$$\Sigma_{\theta\theta} - p_p = \frac{\left(\overset{\infty}{\Sigma}_{xx} - p_p + \overset{\infty}{\Sigma}_{yy} - p_p\right)}{2}\left(1 + \frac{a^2}{r^2}\right) -$$

$$\left(\frac{\overset{\infty}{\Sigma}_{zz} - \overset{\infty}{\Sigma}_{yy}}{2}\right)\left(1 + \frac{3a^4}{r^4}\right)\cos 2\theta -$$

$$\overset{\infty}{\Sigma}_{zy}\left(1 + \frac{3a^4}{r^4}\right)\sin 2\theta - (p_w - p_p)\frac{a^2}{r^2}$$

$$\Sigma_{zz} - p_p = \overset{\infty}{\Sigma}_{zz} - p_p -$$

$$\nu\left[2\left(\overset{\infty}{\Sigma}_{zz} - \overset{\infty}{\Sigma}_{yy}\right)\frac{a^2}{r^2}\cos 2\theta + 4\overset{\infty}{\Sigma}_{xy}\frac{a^2}{r^2}\sin 2\theta\right]$$

$$\Sigma_{r\theta} = -\left(\frac{\overset{\infty}{\Sigma}_{zz} - \overset{\infty}{\Sigma}_{yy}}{2}\right)\left(1 - \frac{3a^4}{r^4} + 2\frac{a^2}{r^2}\right)\sin 2\theta +$$

$$\overset{\infty}{\Sigma}_{zy}\left(1 - \frac{3a^4}{r^4} + \frac{2a^2}{r^2}\right)\cos 2\theta$$

$$\Sigma_{\theta z} = \left(-\overset{\infty}{\Sigma}_{zz}\sin\theta + \overset{\infty}{\Sigma}_{yz}\cos\theta\right)\left(1 + \frac{a^2}{r^2}\right)$$

$$\Sigma_{rz} = \left(\overset{\infty}{\Sigma}_{zz}\cos\theta + \overset{\infty}{\Sigma}_{yz}\sin\theta\right)\left(1 - \frac{a^2}{r^2}\right)$$

In particular, the stress components at the borehole wall are given by:

$$\Sigma_{rr}\Big|_{r=a} = p_w$$

$$\Sigma_{\theta\theta}\Big|_{r=a} - p_p = \overset{\infty}{\Sigma}_{xx} - p_p + \overset{\infty}{\Sigma}_{yy} - p_p - 2\left(\overset{\infty}{\Sigma}_{zz} - \overset{\infty}{\Sigma}_{yy}\right)\cos 2\theta -$$

$$4\overset{\infty}{\Sigma}_{zy}\sin 2\theta - (p_w - p_p)$$

$$\Sigma_{zz}\Big|_{r=a} - p_p = \overset{\infty}{\Sigma}_{zz} - p_p -$$

$$\nu\left[2\left(\overset{\infty}{\Sigma}_{zz} - \overset{\infty}{\Sigma}_{yy}\right)\cos 2\theta + 4\overset{\infty}{\Sigma}_{zy}\sin 2\theta\right]$$

$$\Sigma_{r\theta}\Big|_{r=a} = 0$$

$$\Sigma_{\theta z}\Big|_{r=a} = 2\left(-\overset{\infty}{\Sigma}_{zz}\sin\theta + \overset{\infty}{\Sigma}_{yz}\cos\theta\right)$$

$$\Sigma_{ra}\Big|_{r=a} = 0$$

Note, $\Sigma_{\theta\theta}$ and $\Sigma_{zz}$ are not necessarily principal stresses at the borehole wall. In fact, the principal stresses at $r=a$ are given by the eigenvalues of $$\begin{bmatrix} \Sigma_{rr} & & \\ & \Sigma_{\theta\theta} & \Sigma_{\theta z} \\ & \Sigma_{\theta z} & \Sigma_{zz} \end{bmatrix}\Bigg|_{r=a}$$

That is, the three principal stresses at $r=a$ are $$\left[\frac{1}{2}\left(\Sigma_{\theta\theta} + \Sigma_{zz}\right) \pm \frac{1}{2}\left\{\left(\Sigma_{\theta\theta} - \Sigma_{zz}\right)^2 + 4\Sigma_{\theta z}^2\right\}^{\frac{1}{2}}\right]\Bigg|_{r=a} \quad (1)$$

and $$\Sigma_{rr}\Big|_{r=a}$$

As the mud pressure $p_w$ in the borehole is increased, the stresses in the rocks may become tensile, resulting in fracturing of the rocks and lost circulation problems. An appropriate borehole tensile failure criterion is $$\Sigma_{princ}\Big|_{r=a} - p_p = -T$$

where $\Sigma$ princ =

$$\left[\frac{1}{2}\left(\Sigma_{\theta\theta} + \Sigma_{zz}\right) - \frac{1}{2}\left\{\left(\Sigma_{\theta\theta}\right)^2 + 4\Sigma_{\theta z}^2\right\}^{\frac{1}{2}}\right]$$

With insufficient borehole pressure $p_w$, the compressive strength of the rock is exceeded and the rock fails in compression. This may result in hole enlargement.

Various compressive (or shear) failure criteria have been suggested for rock. If $\sigma_1 \geq \sigma_2 \geq \sigma_3$ are principal stresses, three of the commonest criteria are:

Coulomb: $(\sigma_1 - p_p) - q(\sigma_3 - p_p) = C_o$
Tresca: $\sigma_1 - \sigma_3 = C_o$
and von Mises: $(\sigma_1 - \sigma_2)^2 + (\sigma_2 - \sigma_3)^2 + (\sigma_3 - \sigma_1)^2 = 2C_o^2$ In the borehole situation, $\sigma_1$, $\sigma_2$, $\sigma_3$ are the stresses given at (1).

Figure 2:
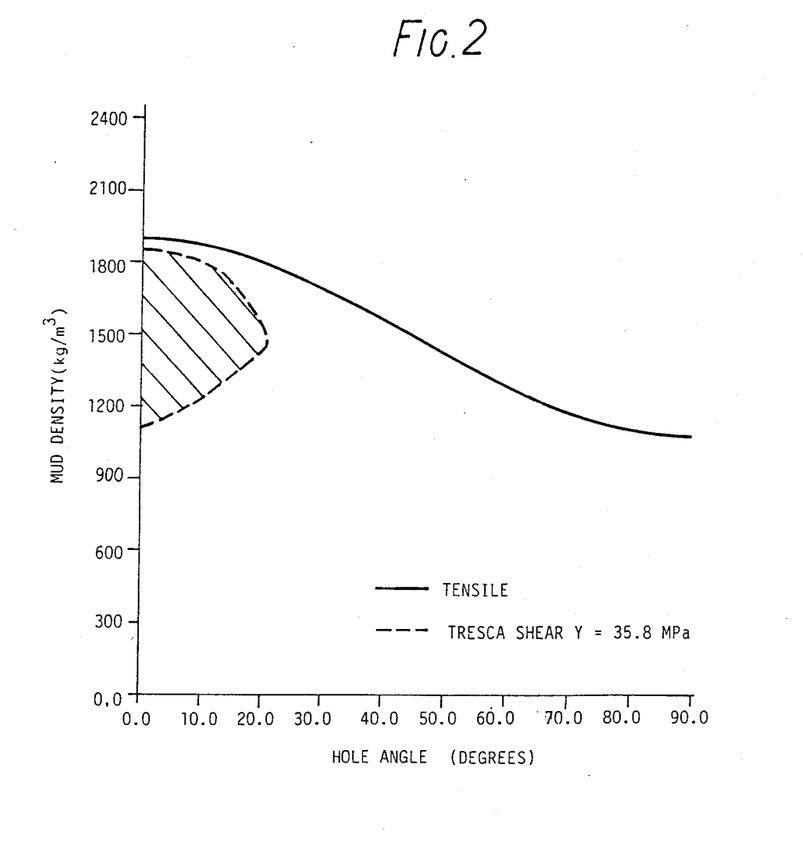
FIGS. 2, 3 and 4 are graphs of mud density versus borehole axis angle relative to true vertical direction in which failure criteria are illustrated.

For the special case of $$\sigma_{zz}{}^\infty = (0.0226 \text{ MPa/m})z$$

$$p_p = (0.0105 \text{ MPa/m})z,$$

where burial has occurred such that $$E\epsilon_{xx}{}^\infty = 0 = \sigma_{xx}{}^{\infty \text{ eff}} - \nu(\sigma_{yy}{}^{\infty \text{ eff}} + \sigma_{zz}{}^{28 \text{ eff}})$$

where $\underline{\sigma}^{eff} = \underline{\sigma} - p_p \mathbf{I}$
and where $\sigma_{yy}{}^\infty = \sigma_{xx}{}^\infty$ is assumed and $\underline{\mathbf{I}}$ is the identity tensor, FIG. 2 shows the mud density in kg/m³ which causes tensile failure at a true vertical depth of 3048 meters as a function of hole deviation in degrees from vertical. The horizontal stresses $\sigma_{xx}{}^\infty$ and $\sigma_{yy}{}^\infty$ are calculated to be 44.4 MPa. Lost circulation will occur at lower mud densities the greater the hole deviation. In this particular case, for example, it is safe (from the lost circulation point of view) to use a 1500 kg/m³ mud in holes of smaller deviation than 45°, but not in holes of greater deviation.

For the in-situ stress state described above, at a depth of 3048 meters, and for a Tresca failure criterion, FIG. 2 shows the region of mud density for which no compressive failure will occur. In this particular example, it is not possible to drill a hole with greater deviation than 21° without compressive failure.

Figure 3:
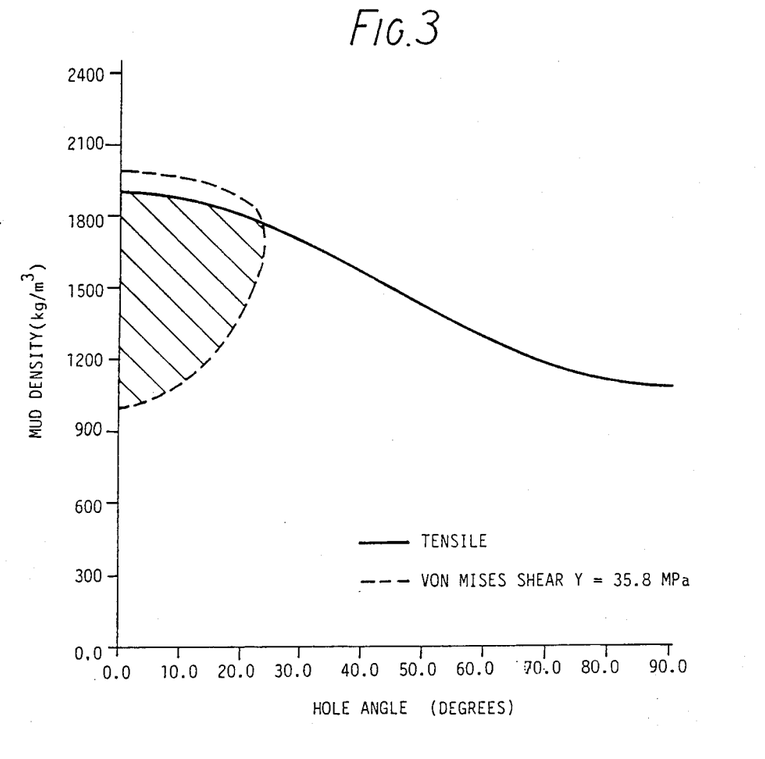

FIG. 3 differs from FIG. 2 only in the form of compressive failure criterion used: FIG. 3 assumes a von Mises criterion.

Figure 4:
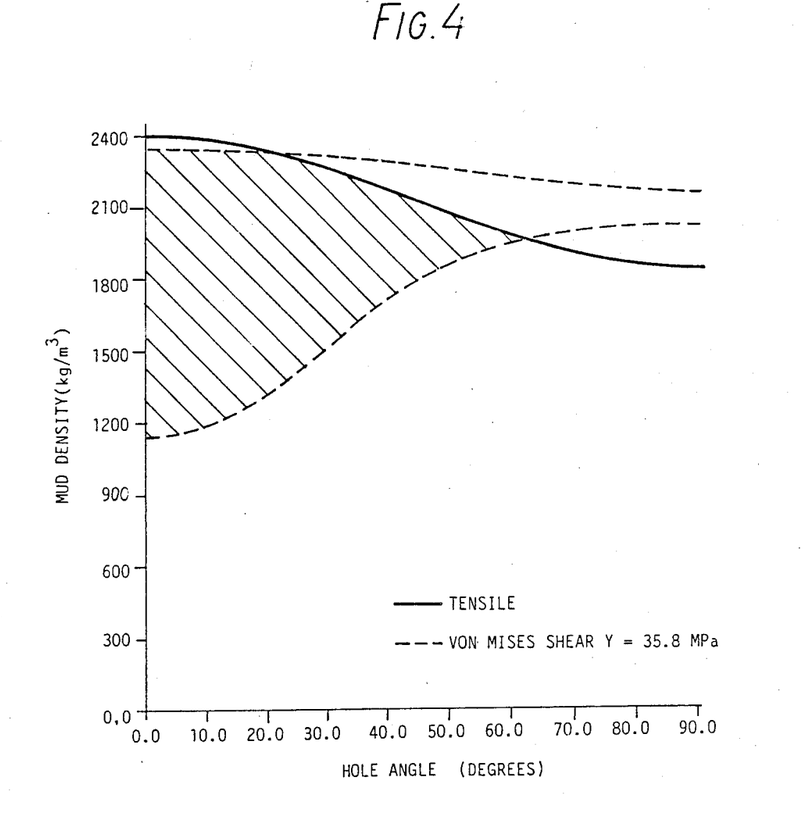

FIG. 4 is plotted using the von Mises criterion but differs from FIG. 3 because different in-situ horizontal stresses are assumed:

$$\sigma_{xx}{}^\infty = \sigma_{yy}{}^\infty = 51.7 \text{ MPa}$$

in FIG. 4, compared with $\sigma_{xx}{}^\infty = \sigma_{yy}{}^\infty = 44.4$ MPa in FIG. 3.

The mud density at which either tensile or compressive failure occurs is extremely sensitive to the assumed value of the in-situ horizontal stresses. Hence reasonably accurate information concerning the in-situ horizontal stresses must be used.

The importance of the curves describing the mud densities at which compressive failure of the borehole wall occurs is that compressive failure may entail massive sloughing, which could be catastrophic to the drilling process. Each curve for mud density at which compressive failure occurs has two parts: one part results from the mud density being too low, whilst the other results from its being too high.

The rock constitutive behaviour and the failure criteria must be correct for the formation(s) being drilled.

The rock compressive strength $C_o$ is the uniaxial compressive strength and is calculated from the expression $$C_o = \frac{a (3.77) E}{C_b \cdot 10^6} [0.008 V_{clay} + 0.0045 (1 - V_{clay})]$$

where $E = \frac{2 \rho_b (1 + \nu)}{dtsm^2}$, $C_b = 1/K_b$, $$K_b = \rho_b \left( \frac{1}{dt^2} - \frac{4}{3 \, dtsm^2} \right)$$

For the Coulomb criterion, $$a = \frac{2 \cos \phi}{1 - \sin \phi}$$

so that for a friction angle of 30°, the value of a for the Coulomb criterion is 3.464.

The Tresca criterion is equivalent to a Coulomb criterion in which a takes the value 2.0.

When one of the three relationships characterising the failure criterion is chosen (either Coulomb or Tresca or von Mises), the critical values of $\rho_m$ as a function of z can be obtained, and, with the trigonometrical correction, a graph of $\rho_m$ against true vertical depth can be plotted.

The value of T in the tensile failure equation $$\left. \Sigma_{princ} \right|_{r=a} - p_p = -T$$

where $\Sigma$ princ is the minimum tangential stress at the borehole wall is calculated from $$T = C_o/12$$

Hence the critical value of $\rho_m$, the mud density, as a function of z can be obtained. Since z in this case is distance measured down the borehole axis, a simple trigonometrical correction is required to convert the values of z into true vertical depth. A graph of $\rho_m$ against true vertical depth can be plotted. Calculated values of failure initiation pressure can be calibrated if leakoff tests have been made in a nearby borehole. A leakoff test is conducted after casing has been set in a borehole. A small length of open hole is drilled beyond the casing and the pressure of the mud in the borehole is increased until a fracture in the uncased portion of the borehole wall is detected. The pressure at which the fracture begins is the fracture initiation pressure. The calculated value of the fracture initiation prssure is also obtained for this borehole and any discrepancy between the measured and calculated values is attributed to incorrect estimation of horizontal stress. The horizontal stress values used in the calculation are calibrated until the calculated and measured fracture initiation pressures are in satisfactory agreement. Use can then be made of caliper data from the borehole subjected to the leakoff test. Caliper data provides meaurement of the borehole diameter. Where the borehole is extremely over gauge, i.e. of much larger diameter than expected from the drill diameter, it is assumed that extensive sloughing has occurred. If the calculated predictions of shear failure of the borehole wall coincide with zones of the borehole which are on gauge, i.e., have the expected diameter, the compressive strength estimate in the calculation is assumed to be too low and is increased until no major discrepancies between the predicted shear failure and the measure borehole diameter exist. Finally, calculation of the mud densities for shear and tensile failure in the intended borehole is carried out using the calibrated data obtained.

FIG. 5(a) is a graph of mud density in kg/m³ against true vertical depth in meters for a planned borehole to be drilled at an angle of 20° to the vertical, showing the mud density values which satisfy the tensile failure criterion $$\left. \sum_{princ} \right|_{r=a} = p_p - T.$$

The values in FIG. 5(a) are calculated from data obtained by logging a nearby borehole.

FIG. 5(b) is a graph of mud density in kg/m³ against true vertical depth in meters showing in the shaded area the region of mud density bounded by an upper limit at which shear failure occurs in accordance with the Coulomb criterion, and a lower limit at which shear failure occurs in accordance with the Coulomb criterion or at which a pore fluid influx occurs, the higher of these two possible lower limits being chosen for each true depth value plotted. The mud density value which provides mud pressure that just balances pore fluid pressure is calculated from the equation $\rho_m gz = 0.0105$ MPa (where z is true vertical depth in meters), or is made equal to the pore fluid density. The values are again calculated from data obtained by logging the nearby borehole.

FIG. 5(c) is a graph of mud density in kg/m³ against true vertical depth in meters showing in the shaded area the region of mud density bounded by the lower limit of FIG. 5(b), and the lower of the higher limit of FIG. 5(b) and the value from FIG. 5(a).

Figure 5:
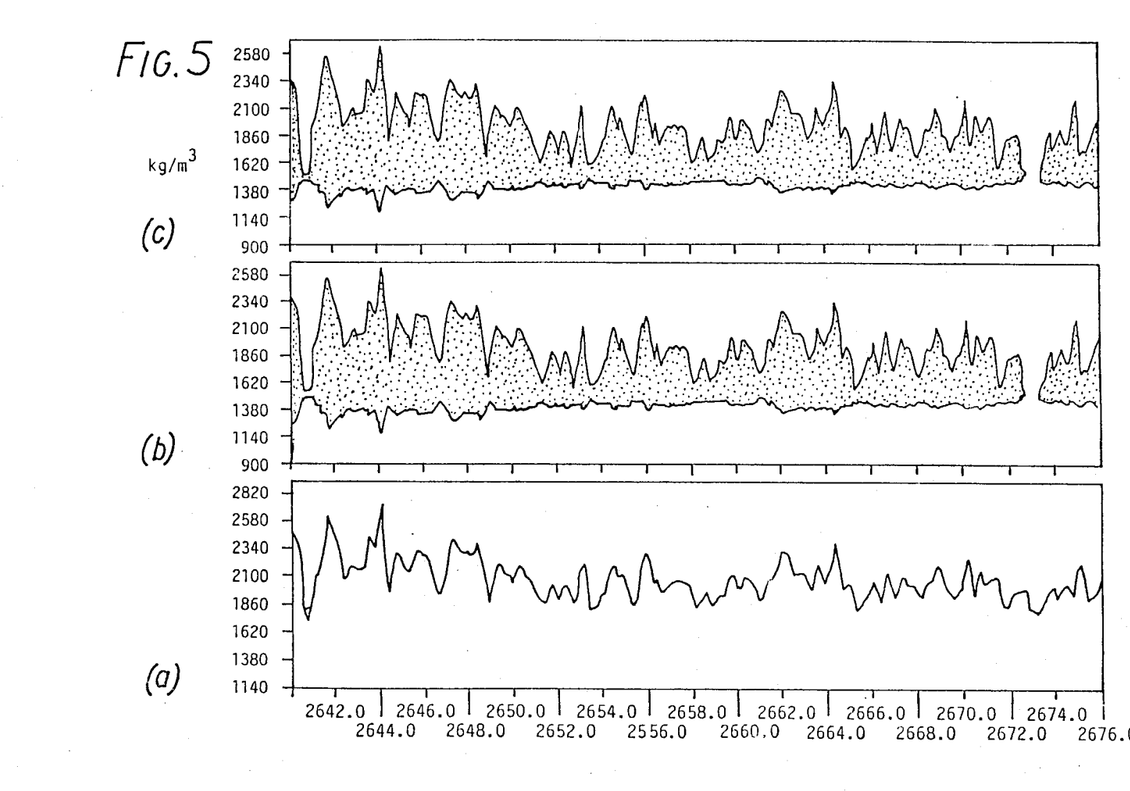
Figure 6:
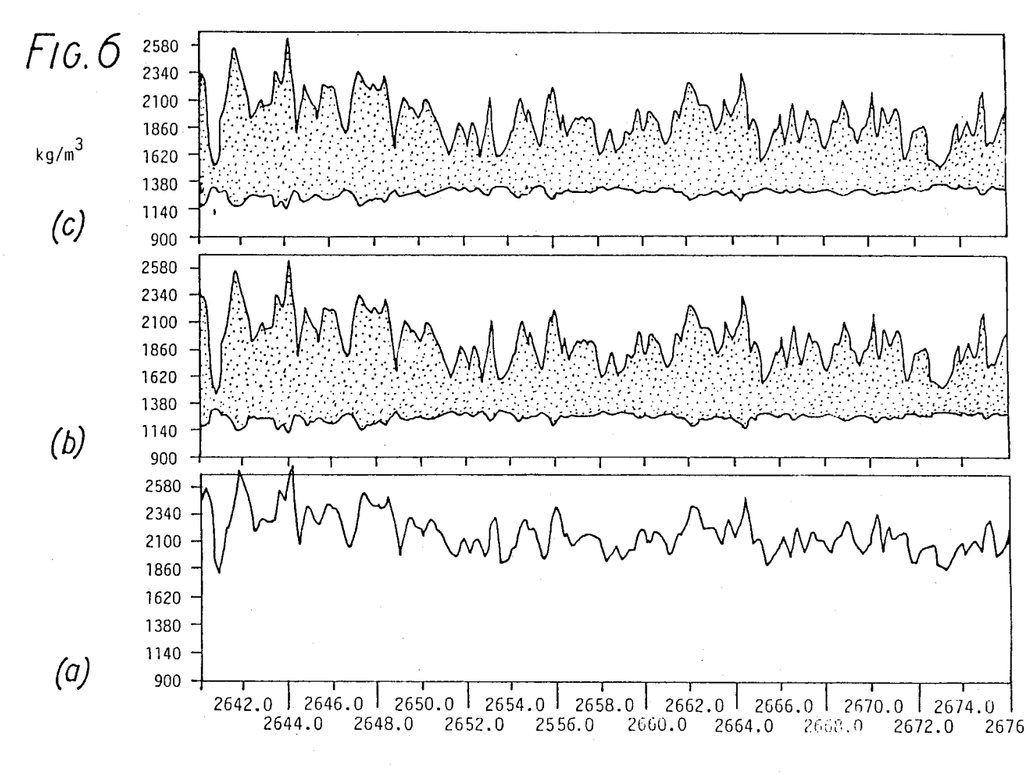

FIG. 6 shows at (a), (b) and (c) the same graphs as FIGS. 5(a), (b) and (c) respectively but calculated for the logged vertical nearby borehole, or for an intended vertical borehole.

A leakoff test was conducted in the logged borehole at 2657.5 meters and gave a mud density of 2277 kg/m³ FIG. 6(a) predicts a mud density of 2169 kg/m³ to give the fracture initiation pressure at 2657.5 meters. The measured density of 2277 kg/m³ was used to calculate the horizotal stress actually existing at the borehole wall at 2657.5 meters. This calculated horizontal stress was then used to calibrate the horizontal stress values predicted by the logged data, and these calibrated values were used in the calculations for the planned borehole to produce the graphs of FIGS. 7(a), (b) and (c) which are mud density values in kg/m³ against depth in meters for tensile failure, shear failure or pore fluid influx, and the combined limits respectively, as in FIG. 6.

It will be seen from FIG. 5 that the graphs of FIG. 5(b) and FIG. 5(c) include short regions at a depth of approximately 2673 meters over which there is no mud density at which shear failure does not occur. At such regions, the graphs indicate that, for any mud density chosen to prevent an influx of pore fluid, the borehole will inevitably collapse at this depth. Depending upon the volume of material which would slough from those regions, it may be necessary to chose some other angle of inclination.

Figure 7:
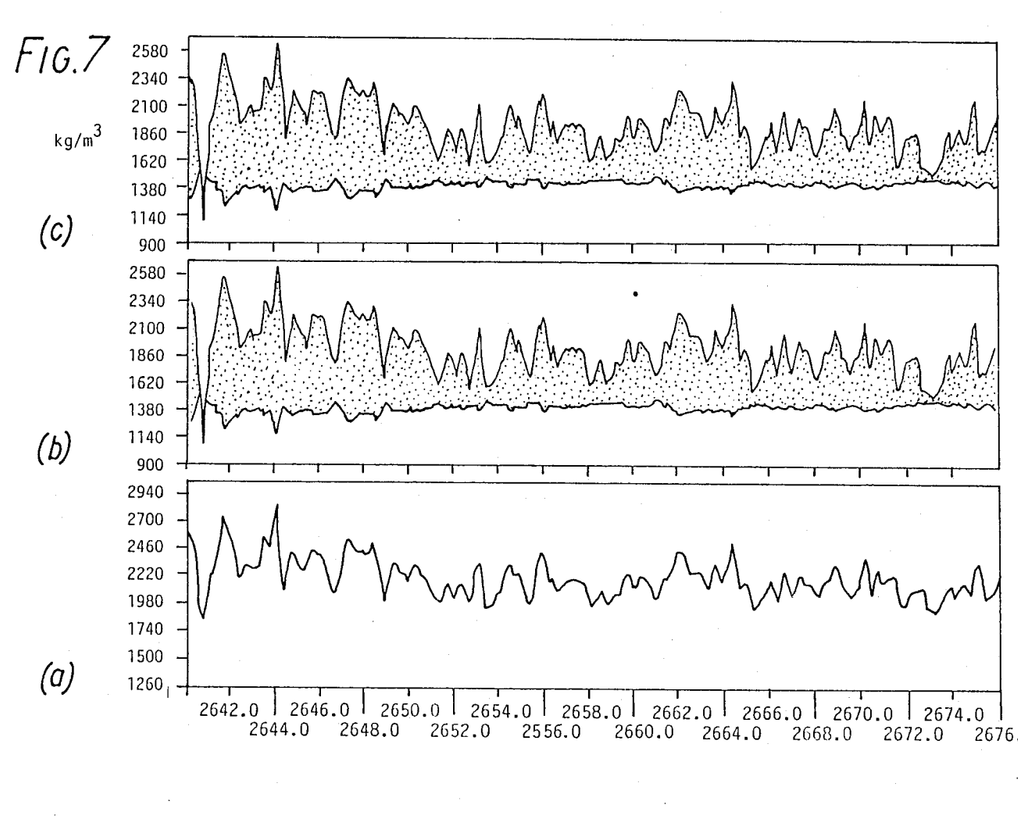

The graphs of FIGS. 5, 6 and 7 can be produced automatically by means of a computing system with graphical plotting equipment arranged to provide a three track log as output, the three tracks corresponding respectively to the three parts (a), (b) and (c) of these graphical illustrations. The computing system is programmed with a first algorithm to produce critical mud density values as a function of true vertical depth, in accordance with the tensile failure criterion, thereby producing the data for the (a) track of the graphical output, a second algorithm to produce lower and upper limits of mud density value as a function of true vertical depth in accordance with a chosen shear failure criterion and t avoid pore fluid influx, thereby producing the data for the (b) track of the graphical output, and a simple third algorithm comparing the tensile failure mud density values with the shear failure or pore fluid influx mud density values as a function of true vertical depth to produce the data for the (c) track of the graphical output.

A safe value of mud density, i.e., a value which will not result in tensile failure or shear failure of the walls or pore fluid influx, can be chosen by finding on the graph (c) for the planned borehole a value of mud density which is within the upper and lower limits on this graph for all values of true vertical depth. Such a value corresponds to a line parallel to the depth axis and lying within the shaded area over its entire length. Obviously, it is preferable to use FIG. 7(c) rather than FIG. 5(c).

The density of the mud in the mud pits 14 is made up to the safe value thus determined before drilling starts, and is maintained at the safe value by making whatever additions of solid material or liquid material are required. The density of the mud must be monitored throughout drilling.

I claim:
1. A method for improving the process of drilling a deviated borehole through a subsurface formation by determining a safe value of the density of drilling fluid to be circulated through the borehole while the deviated borehole is being drilled, the method comprising the steps of:
   a. determining the in-situ stress state of the formation at the site of the borehole,
   b. converting the in-situ stress state of step a. into the stresses that exist in the projected direction of the borehole axis and in two orthogonal directions perpendicular to that borehole axis;
   c. in response to step b. and to an assumed drilling fluid density, calculating the stress which will occur at the borehole wall as a function of depth when the borehole is drilled,
   d. determining formation pore pressure as a function of depth,
   e. in response to step c, determining the value of drilling fluid density at a given depth which satisfies a tensile failure criterion of the material forming the borehole wall,
   f. in response to step c, determining at least one value of drilling fluid density at said given depth which satisfies a shear failure criterion of the material forming the borehole wall,
   g. in response to step d, calculating a drilling fluid density value which gives drilling fluid pressure equal to the formation pore pressure as a function of depth,
   h. at said given depth, in response to at least the valve obtained in step (e), determining a maximum value for the drilling fluid density,
   i. at said given depth, selecting as a minimum value for the drilling fluid density, the higher of the values obtained at that depth in steps f and g, and
   j. mixing solid and liquid drilling fluid components in such proportion that the density of the drilling fluid lies between the selected valvues of steps h and i.

2. A method according to claim 1, wherein the depth is the true vertical depth.

3. A method according to claim 1 or 2, wherein the step of determining the in-situ stress state includes logging a neighbouring drilled borehole and utilizing the logged data in calculating vertical and horizontal stress values and in calculating uniaxial compressive strength and tensile strength values.

4. A method according to claim 3, wherein at least one in-situ stress is measured in the said neighbouring borehole and the measured stress value is used to calibrate corresponding calculated stress values for the borehole to be drilled.

5. A method according to claim 3, wherein at least one fracture initiation pressure is measured in the said neighbouring borehole and the measured value is used to calibrate stress values calculated as occurring at the wall of the to be drilled borehole.

6. A method according to claim 3, wherein caliper data are acquired in at least a portion of the neighboring drilled borehole and the caliper data are utilized in calibrating the compressive strength values.

7. A method according to claim 1 wherein the step of determining the values of drilling fluid density as a function of depth includes the production of graphical representations of the density values satisfying the tensile failure criterion as a function of depth, and the density values satisfying a chosen shear failure criterion as a function of depth.

8. A method according to claim 7, wherein the step of determining the upper and lower values of drilling fluid density as a function of depth includes the step of producing a graphical representation of all density values which fall between the said one and the other failure criterion as a function of depth.

9. A method according to claim 1 wherein at said given depth a high and a low value of drilling fluid density satisfying a shear failure criterion of the material forming the borehole wall are determined, said method further comprising the steps of: -comparing at said depth said high value with the value determined in step e of claim 11 and selecting the lower of the two values of drilling fluid density, and -comparing at said depth said low value with the value calculated in step g of claim 11 and selecting the higher of the two values of drilling fluid density.

* * * * *